(12) United States Patent
Bhan et al.

(10) Patent No.: US 6,887,990 B1
(45) Date of Patent: May 3, 2005

(54) METHOD FOR DEPROTECTING OLIGONUCLEOTIDES

(75) Inventors: Anila Bhan, Belle Mead, NJ (US); Lars Holmberg, Whitefish Bay, WI (US)

(73) Assignee: Amersham Biosciences Corp, Piscataway, NJ (US)

( * ) Notice: Subject to any disclaimer, the term of this patent is extended or adjusted under 35 U.S.C. 154(b) by 0 days.

(21) Appl. No.: 09/498,773

(22) Filed: Feb. 5, 2000

Related U.S. Application Data
(60) Provisional application No. 60/118,575, filed on Feb. 5, 1999.

(51) Int. Cl.[7] .............................................. C07H 21/00
(52) U.S. Cl. .................................................. 536/25.31
(58) Field of Search ...................................... 536/25.31

(56) References Cited

U.S. PATENT DOCUMENTS

| | | | | |
|---|---|---|---|---|
| 4,417,046 A | * | 11/1983 | Hsiung ..................... | 536/25.33 |
| 4,426,517 A | * | 1/1984 | Hsiung ..................... | 536/25.31 |
| 4,672,110 A | | 6/1987 | Letsinger ................. | 536/25.31 |
| 4,835,263 A | * | 5/1989 | Nguyen et al. ............ | 536/23.1 |
| 5,362,866 A | | 11/1994 | Arnold, Jr. ................. | 536/25.3 |
| 5,936,077 A | | 8/1999 | Pfleiderer et al. .......... | 536/23.1 |
| 6,127,533 A | * | 10/2000 | Cook et al. ................ | 536/23.1 |
| 6,465,628 B1 | * | 10/2002 | Ravikumar et al. ........ | 536/23.1 |

FOREIGN PATENT DOCUMENTS

| | | | |
|---|---|---|---|
| EP | 1028124 A2 | * | 8/2000 |
| JP | 62-042997 A | * | 2/1987 |
| WO | WO 92/09615 | | 6/1992 |
| WO | WO9835978 A1 | * | 8/1998 |

OTHER PUBLICATIONS

Hsiung et al., "Further Improvements on the Phosphodiester Synthesis of Deoxyribonucleotides and the Oligonucleotide Directed Site–Specific Mutagenesis of *E. coli* Lipoprotein Gene," Nucleic Acids Research, 11(10), 3227–3239 (May 25, 1983).*

Ohtsuka et al. (I), "Studies on Transfer Ribonucleic Acids and Related Compounds. XVL. Synthesis of Ribooligonucleotides Using a Photosensitive o–Nitrobenzyl Protection for the 2'–Hydroxyl Group," Chemical & Pharmaceutical Bulletin (*Japan*), 25(5), 949–959 (May, 1997).*

Ohtsuka et al. (II), "Synthesis of *E. coli* tRNA$_f^{Met}$ Fragments," presented at the Fourth Symposium on Nucleic Acid Chemistry, Kyoto, Japan, Nov. 26–27, 1976, *Nucleic Acids Research Symposium Series, Special Publication No. 2*, E. Coast (ed.), IRL Press, Ltd, London, England, pp. s77–s80 (1976).*

Beaucag, S. L., et al.; The Synthesis of Modified Oligonucleotides by the Phosphoramidite Approach and Their Applications; Tetrahedron, vol. 49, No. 28, (1993), pp. 6123–6194.

Matteucci, M. D., et al.; The Synthesis of Oligodeoxypyrimidines on a Polymer Support; Tetrahedron, vol. 21, (1980), pp. 719–722.

Solomon, J. J., et al.; In Vitro Alkylation of Calf Thymus DNA by Acrylonitrile. Isolation of Cyanoethyl–Adducts of Guanine and Thymine and Carboxyethyl–Adducts of Adenine and Cytosine; Chem–Biol Interactions, vol. 51 (1984), pp. 167–190.

Griffin, L. C., et al.; The Discovery and Characterization of a Novel Nucleotide–Based Thrombin Inhibitor; Gene, vol. 137 (1993), pp. 25–31.

Jin, L., et al.; In Situ Hybridization: Methods and Applications; Journal of Clinical Laboratory Analysis, vol. 11 (1997), pp. 2–9.

Alams, A., et al.; Antisense Oligonucleotides as Therapeutic Agents; Pharmacological Research, vol. 36, No. 3 (1997), pp. 171–178.

Tasset, D. M., et al.; Oligonucleotide Inhibitors of Human Thrombin that Bind Distinct Epitopes; Journal of Molecular Biology, vol. 272 No. 5 (1997), pp. 688–698.

Gait, M. J., et al.; Rapid Synthesis of Oligodeoxyribonucleotides: A New Solid Method; Nucleic Acids Research, vol. 4 No. 4 (1977), pp. 1135–1158. (Apr., 1977).

Shchepinov, M. S., et al.; Oligonucleotide Dendrimers: Synthesis and Use as Polylabelled DNA Probes; Nucleic Acids Research, vol. 25 No. 22 (1997), pp. 4447–4454.

Bonora, G. M., et al.; HELP (High Efficiency Liquid Phase) New Oligonucleotide Synthesis on Soluble Polymeric Support; Nucleic Acids Research, vol. 18, No. 11 (1990), pp. 3155–3159.

Koster, H.; Polymer Support Oligonucleotide Synthesis VIII Use of Polyethylenglycol; Tetrahedron Letters, vol. 16 (1972), pp. 1535–1538. (Issue No. 16).

Ravikumar, V.T., et al.; 4–Cyano–2–Butenyl Group: A New Type of Protecting Group in Oligonucleotide Synthesis Via Phosphoramidite Approach; Nucleosides and Nucleotides, vol. 16 No. 7 9 (1997), pp. 1709–1712.

(Continued)

*Primary Examiner*—L. E. Crane
(74) *Attorney, Agent, or Firm*—Royal N. Ronning, Jr.; Stephen G. Ryan; Yonggang Ji

(57) ABSTRACT

A method for purifying an oligonucleotide that comprises providing an oligonucleotide attached to a substrate, wherein the oligonucleotide contains phosphate protecting groups; contacting the oligonucleotide with a reagent, e.g., an organic amine, that cleaves the phosphate protecting groups from the oligonucleotide without detaching the oligonucleotide from the substrate; isolating the oligonucleotide attached to the substrate from the cleaved phosphate protecting groups; and cleaving the oligonucleotide from the substrate. This method provides crude oligonucleotide mixtures that are easier to purify and from which the desired full-length oligonucleotide product can be isolated in higher yields.

15 Claims, 4 Drawing Sheets

OTHER PUBLICATIONS

Temsamani, J., et al.; Sequence Identity of the n–1 Product of a Snythesis Oligonucleotide; Nucleic Acids Research, vol. 23 No. 11 (1995), pp. 1841–1844.

Wilk, A., et al.; The 4–[N–Methyl–N–(2,2,2–trifluoroacetyl)amino]butyl Group as an Alternative to the 2–Cyanoethyl Group for Phosphate Protection in the Synthesis of Oligodeoxyribonucleotides; Journal of Organic Chemistry, vol. 64 (1999), pp. 7515–7522.

Reese, C. B., et al.; A New Approach to the Synthesis of Oligonuceotides and Their Phosphorothioate Analogues in Solution; Bioorganic and Medicinal Chemistry Letters, vol. 7, No. 21 (1997), pp. 2787–2792.

Gold, L., et al.; From Oligonucleotide Shapes to Genomic SELEX: Novel Biological Regulatory Loops; Proc. National Academy of Sciences USA, vol. 94 (1997), pp. 59–64. (Jan., 1997).

Mag, M., et al., Synthesis and Structure Assignments of Amide Protected Nucleosides and Their Use as Phosphoramidites in Deoxyoligonucleotide Synthesis; Nucleic Acids Research, vol. 16, No. 8 (1988), pp. 3525–3543.

Crea, R., et al.; Synthesis of Oligonucleotides on Cellulose by a Phosphotriester Method; Nucleic Acids Research, vol. 8 No. 10 (1980), pp. 2331–2348.

* cited by examiner

METHOD FOR DEPROTECTING OLIGONUCLEOTIDES

CROSS-REFERENCE TO RELATED APPLICATIONS

This application claims priority to U.S. Provisional Application Ser. No. 60/118,575, filed on Feb. 5, 1999, the entire disclosure of which is incorporated entirety herein.

BACKGROUND OF THE INVENTION

1. Field of the Invention

The instant disclosure pertains to a method for synthesizing oligonucleotides. In particular, this disclosure pertains to a method for deprotecting oligonucleotides which results in a higher yield of crude oligonucleotide product with greatly improved purity.

2. Background

Oligonucleotides find enormous utility in a number of biological applications. For example, oligonucleotide sequences form duplexes with complementary oligonucleotide targets and can be used as molecular biological probes in genome research and in clinical diagnostic applications involving disease causing genes. In this application, materials containing a nucleic acid to be detected are brought in contact with an oligonucleotide probe which forms a duplex with its complementary nucleic acid sequence. The duplex is then detected using various analytical techniques.

Oligonucleotides also find utility as primers for various polymerase applications such as the polymerase chain reaction ("PCR"). In PCR, an oligonucleotide primer is added to a sample containing single stranded template nucleic acid fragments in the presence of an enzyme and mononucleotides. Starting at the primer, the enzyme builds a nucleic acid strand which is complementary to the template nucleic acid. The reaction is carried out several times in succession where in each cycle the newly built strand is amplified.

Oligonucleotides have also been used as a combinatorial discovery tool to design oligonucleotide sequences that act as competitive inhibitors of certain disease causing and unwanted proteins. In this application, also known as the "aptamer approach," the high affinity of a particular protein of interest with a specific oligonucleotide sequence present in a random pool of millions of randomly synthesized oligonucleotide sequences is determined. This technique has been instrumental in developing novel oligonucleotide inhibitors of various proteins such as thrombin.

Oligonucleotides have even been found to have the capability to modulate gene expression at the messenger RNA level ("antisense") or at the DNA level ("antigene" or "triplex"). The efficacy of a large number of oligonucleotide candidates is presently under clinical evaluation.

Given the significant therapeutic, diagnostic, and research utility of oligonucleotides, there is a need to prepare them in large quantities easily, quickly and at low cost. Phosphite triester and H-phosphonate chemistries are commonly used to prepare oligonucleotides on a solid support or substrate. Large scale commercial DNA synthesizers that employ phosphite triester chemistry, has made the production of multi-kilo grams of oligonucleotides possible.

Nucleosides used in large scale synthesis of oligonucleotides on a solid phase by phosphoramidite chemistry use are protected with suitable groups that prevent formation of side products during oligonucleotide synthesis. The reactive exocyclic amine groups found on the nucleobases in monomer building blocks are generally protected with benzoyl, isobutyrl, phenoxyacetyl, and acetyl protecting groups, while the phosphate groups are usually protected as 2-cyanoethyl phosphoramidites. Such protective groups are easily removed after completion of the oligonucleotide synthesis by treatment with a concentrated solution of is ammonium hydroxide.

Oligonucleotide synthesis begins by attaching a suitably protected, 5'-O-dimethoxytritylated nucleoside to a substrate. The 3'-hydroxyl group of the protected nucleoside is connected via a succinic ester linkage to the substrate. The most commonly used substrates are inorganic materials such as long chain glass or organic supports such as polystyrene; however, other supports such as polyamide, cellulose, silica gel, and polyethylene glycols, are also used in the solid phase synthesis of oligonucleotides.

The oligonucleotide is assembled by sequential addition of 5'-dimethoxytritylated-3'nucleoside phosphoramidites to the unmasked 5'-hydroxy group of the first nucleoside loaded on to the support. This addition is catalyzed by a mildly acidic catalyst such as tetrazole or dicyanoimidazole. The corresponding phosphite triester ("$P^{III}$") internucleotide linkage is then converted to a more stable phosphate triester ("$P^V$") by oxidation with iodine or peroxides. "Capping" of any unreacted 5'-hydroxyl groups by converting them to corresponding esters is achieved by a brief exposure to capping reagents containing acetic anhydride. Next, removal of 5'-dimethoxytrityl group from the newly added nucleoside under mildly acidic conditions generates the 5'-hydroxyl group and completes the coupling cycle. Using this method, a coupling efficiency of greater than 99% in each coupling step can be achieved. Towards the end of oligonucleotide synthesis, the dimethoxytrityl group of the terminal nucleotide at the 5'-end is either left intact ("trityl-on") or cleaved to give an oligonucleotide with free 5'-terminal hydroxyl group ("trityl-off"). The 5'-trityl group may be used as a lipophilic purification handle to purify the full length oligonucleotide bearing the trityl group from shorter and non-tritylated oligonucleotide species by reverse HPLC.

After completion of oligonucleotide synthesis, the succinic ester linkage is cleaved under alkaline conditions to release the oligonucleotide from the substrate in addition to the removal of protective groups from the nucleobases and the phosphate backbone. This is achieved by treating the substrate with a concentrated solution of ammonium hydroxide. This process usually takes about 24 hours at room temperature or about 6 hours at 55° C.

One of the major problems associated with stepwise coupling of mononucleotides phosphoramidites is the formation of shorter deletion sequences during oligonucleotide synthesis. This population of unwanted failure sequences ("n−1," "n−2," etc.) results from less than 100% coupling efficiency of the phosphoramidites, incomplete capping and oxidation or partial unmasking of the 5'-hydroxyl group before the initiation of the next coupling cycle.

Frequently observed, but least addressed are the so called "n+1" or "n+2" oligonucleotide impurities that are seen to elute immediately after the main oligonucleotide peak on HPLC columns. These unwanted impurities can comprise up to 6% of the total crude product cleaved from the substrate. Little is known about the nature and cause of these impurities. The elution of these impurities close to the main product makes the isolation of the purified oligonucleotide a difficult and time-consuming task and results in a poor recovery of the full length pure product.

As the above discussion suggests, improvements are still possible and desirable in the area of oligonucleotide synthesis. In particular, a method is needed for synthesizing oligonucleotides which results in a high yield of purer crude product. Ideally, such a method would not involve increased synthesis time. Preferably, such a method would also be economical to use. These and other concerns are addressed in greater detail below.

SUMMARY OF THE INVENTION

Figure 1:
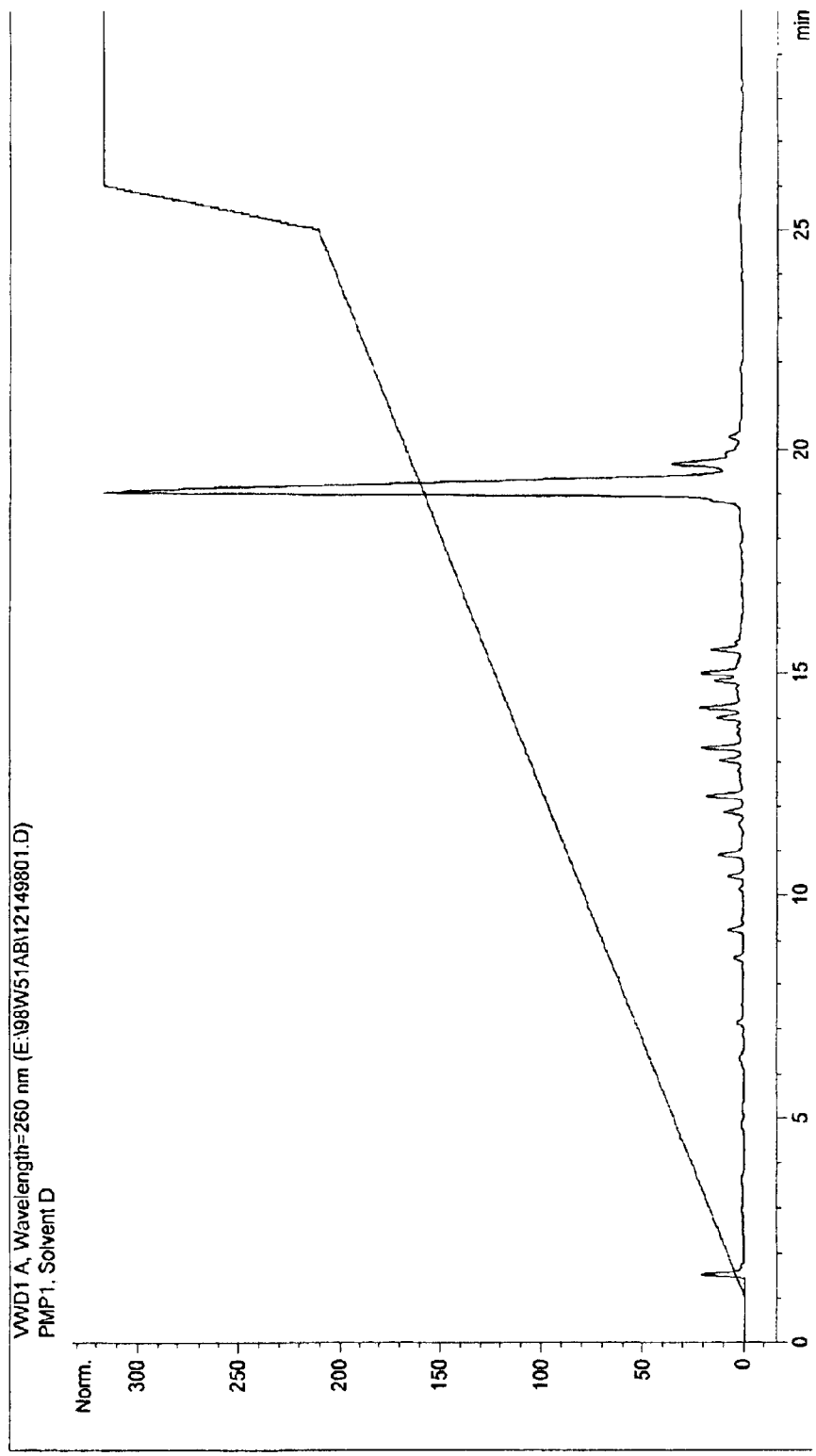
FIG. 1 is a chromatogram of a crude trityl-on oligonucleotide $T_{10}G_{10}$ mixture separated by HPLC and detected at 260 nm.

The instant disclosure pertains to a method for purifying an oligonucleotide that comprises providing an oligonucleotide attached to a substrate, wherein the oligonucleotide contains phosphate protecting groups; contacting the oligonucleotide with a reagent that cleaves the phosphate protecting groups from the oligonucleotide without detaching the oligonucleotide from the substrate; isolating the oligonucleotide attached to the substrate from the cleaved phosphate protecting groups; and cleaving the oligonucleotide from the substrate.

Preferably, the phosphate protecting group is a group capable of undergoing β-elimination, such as 2-cyanoethyl. The reagent cleaves the phosphate protecting group from the oligonucleotide by β-elimination. Preferably, the reagent comprises an amine with a formula R—N—$R_1R_2$ wherein R, $R_1$ and $R_2$ are independently hydrogen, hydroxy, alkyl, allyl, aryl, cycloalkyl, alkenyl, alkoxy, allyloxy, aryloxy, and may include from one to twenty carbon atoms.

In particular, the instant disclosure pertains to a method for purifying an oligonucleotide that comprises providing an oligonucleotide containing a phosphate protecting group attached to a substrate, wherein the phosphate protecting group is 2-cyanoethyl; contacting the oligonucleotide with diethylamine to cleave the phosphate protecting groups from the oligonucleotide without detaching the oligonucleotide from the substrate; isolating the oligonucleotide attached to the substrate from the cleaved phosphate protecting groups; and contacting the oligonucleotide attached to the substrate with ammonium hydroxide to cleave the oligonucleotide from the substrate.

DETAILED DESCRIPTION

Oligonucleotides are typically assembled on a solid support or substrate, either manually or using an automated DNA synthesizer, and released from the substrate under alkaline deprotection conditions. Many groups commonly used to protect the phosphate backbone, e.g., 2-cyanoethyl, produce reactive intermediates during standard deprotection process in which an alkali, such as ammonium hydroxide, is used both to remove the protecting groups from the oligonucleotide as well as detach the oligonucleotide from the substrate. Such intermediates have been observed to modify oligonucleotides by reacting irreversibly with nucleobases resulting in the formation of higher molecular weight oligonucleotide side products. While theoretically side chain branching can give rise to these 3 higher molecular weight species, base composition analysis does not support this hypothesis (see Example 1, infra).

In the phosphoramidite method for oligonucleotide synthesis, the most common protecting group used for the phosphate protection is the 2-cyanoethyl protecting group. This group is removed along with the protecting groups on nucleobases by treatment with concentrated ammonium hydroxide. Under these conditions, 2-cyanoethyl group undergoes β-elimination with the release of acrylonitrile. Acrylonitrile has shown to be a potent carcinogen capable of irreversible alkylation of nucleobases. Therefore, it is possible that acrylonitrile released from phosphate deprotection can, in principle, react with the nucleobases in oligonucleotides and result in their unwanted modification. Given that standard oligonucleotide deprotection protocol involves relatively long exposure of the ammonium hydroxide solution with oligonucleotide bearing substrate (6–24 hr), acrylonitrile can easily react with nucleobases during this time in solution and result in observed n+1 and n+2 oligonucleotide modifications. This is especially true in large scale synthesis of oligonucleotide on substrate, where for economical and practical reasons, reduced solvent volumes are used and where reduced volumes can easily result in higher concentration of acrylonitrile in deprotection solutions thereby facilitating the irreversible modification of nucleobases. These higher molecular weight species that often elute closely to the main oligonucleotide peak in High Pressure Liquid Chromatography (HPLC) make the purification of the oligonucleotide a very difficult and inefficient process where a lot of oligonucleotide remains impure do to these closely eluting impurities. A method that can reduce the exposure of acrylonitrile with oligonucleotides during deprotection can, therefore, minimize the modification of nucleobases.

We have found that this can be achieved by contacting the oligonucleotide attached to a substrate with a reagent that can rapidly and selectively remove phosphate protecting groups while the oligonucleotide is still tethered to the substrate. This ensures that acrylonitrile in the reagent solution can simply be siphoned off quickly while the oligonucleotide is still attached to the substrate, thereby minimizing the exposure of nucleobases to acrylonitrile. After removal of the acrylonitrile containing reagent solution, the substrate can be next treated with concentrated ammonium hydroxide to release the oligonucleotide from the substrate with concomitant removal of other protecting groups.

By "oligonucleotide" is meant to include both standard and modified oligoribonucleotides, oligodeoxyribonucleotides, oligopurines, oligopyrimidine, and analogs or combinations thereof. Examples are regular and modified DNA, RNA, and combinations thereof. The oligonucleotide may be comprised of bases such as a common nucleoside purine or pyrimidine base capable of hydrogen bonding or/and stacking and can be selected as adenine, guanine, cytosine, thymine, uracil or a substituted purine or pyrimidine base. Such bases are usually attached to the sugar at the 9-position of the purine, but may also be attached at the 7-position. In pyrimidines, the sugars are attached at the I-position of the base. Substituted bases include, but are not necessarily limited to, 5-methyl cytosine, 6-thioguanine, nitro indoles, 8-azidoadenine, 8-aminoadenine, 8-mercaptoadenine, 8-azaguanine, 8-deazaguanine, 5-fluorouracil, diaminopurine. Sugars include, pentoses, hexoses, tetroses and trioses. Natural sugars include β-D-ribofuranose, 3' or 2'-deoxy ribofuranose or such unnatural sugars as L-sugars. The glycosidic linkage is normally the naturally occurring β-anomeric form but may also include the α-anomeric configuration about the glycosidic bond. Modified sugars include but are not necessarily limited to derivatized β-D-ribofuranosyl, 3'/2'-deoxy β-ribofuranosyl, conformationally restricted sugars and carbocyclic sugars. The methods used to prepare these derivatives are well known to those skilled in the art.

Nucleosides used in large scale synthesis of oligonucleotides by phosphoramidite chemistry are usually protected with suitable groups that prevent the formation of side products during oligonucleotide synthesis. The reactive exocyclic amine groups found on the nucleobases in monomer building blocks are generally protected with benzoyl, isobutyrl, phenoxyacetyl, and acetyl protecting groups, while the phosphate groups are usually protected as 2-cyanoethyl phosphoramidites. In addition, there are many other phosphate protecting groups available that also undergo 5-elimination giving rise to possible reactive intermediates that can potentially modify nucleobases in oligonucleotides (Ravikumar, V. T.; Cheruvallath, Z. S. & Cole, D. L. (1997), Nucleosides & Nucleotides, vol. 16 (7–9) 1709–1712; Beaucage, S. L & Iyer, R. P. (1993) Tetrahedron, 49 (28), 6123–6194). Such protecting groups if removed selectively with reagents that minimize interaction of the said intermediates with oligonucleotides would follow within the scope of this invention.

The substrate system on which the oligonucleotide is attached may be selected from a wide range of both organic as well as inorganic materials such as controlled pore glass and various glasses, silica gel, polyamides, polystyrenes, cross-linked polystyrenes, polysaccharides, cross-linked polysaccharides and combinations thereof. In general, the substrate should be stable to all the conditions of oligonucleotide and modified oligonucleotide synthesis. A wide range of porous and non-porous substrates that have the capacity to swell or not swell may be used in the present invention. While in a preferred embodiment the substrate is comprised of a solid substance, substrates that exist as liquids or solids (depending on the reaction environment) may also be included in the present invention. (Bonora, G. M.; Scremin, C. L.; Colonna, F. P. & Garbesi, A. (1990) Nucleic Acids Research, vol. 18 (11), 3155–3159). Preferably, the substrate is a solid substance, as the kinetics of irreversible modification of nucleobases with acrylonitrile may be slower when the oligonucleotide is still attached to the substrate rather than being in solution. Preferably, the substrate is contained within a reaction column.

After completion of oligonucleotide synthesis using any available method such as phosphite triester and H-phosphonate chemistries, the substrate-bound oligonucleotide is treated with a reagent to selectively remove the phosphate protecting groups from the oligonucleotide backbone. The selection of reagent and conditions thereof is generally dependent on the ability of the reagent to selectively cleave the phosphate protecting groups in such a manner that the oligonucleotide still remains attached to the substrate. Any compound or enzyme that can achieve this effect falls within the scope of the present disclosure. For example, many phosphate protecting groups such as 2-cyanoethyl are capable of undergoing β-elimination. Accordingly, any reagent capable of cleaving the phosphate protecting group from the oligonucleotide by β-elimination may be used. Organic amines such as primary, secondary or tertiary amines that can remove the phosphate protecting group without cleaving the oligonucleotide from the substrate are preferred. More preferred are amines with the formula R—N—$R_1R_2$, wherein R, $R_1$ and $R_2$ are independently hydrogen, hydroxy, alkyl, allyl, aryl, cycloalkyl, alkenyl, alkoxy, allyloxy, aryloxy, and may include from one to twenty carbon atoms. Most preferred are t-butylamine-methylamine and diethylamine, in particular a solution of about 20% v/v diethylamine in anhydrous acetonitrile.

The reagent may be introduced into the reaction as a liquid or more preferably as a gas. The process can take place manually in a reaction vessel. Preferably, the process is automated using a commercial DNA synthesizer programmed to deliver the amine containing reagent in liquid or in gas phase through one of the delivery lines of the synthesizer after the completion of last coupling cycle. Preferably, the reagent is passed through a reaction column at a flow rate of about 1 ml/min for about 10 minutes at 65° C. (or 90 min at room temperature) to selectively remove the phosphate protecting groups. Alternatively, the reagent may be passed through a reaction column at a flow rate of about 1 ml/min for about 90 minutes at room temperature to selectively remove the phosphate protecting groups.

Any acrylonitrile in the reagent solution is siphoned off quickly while the oligonucleotide is still attached to the substrate, thereby minimizing the exposure of nucleobases to acrylonitrile. Preferably, this step is followed by washing of the substrate with solvent such as acetonitrile to remove any last traces of acrylonitrile. The oligonucleotide and substrate are then treated with concentrated ammonium hydroxide to release the oligonucleotide from the substrate along with the concomitant removal of other protecting groups.

The instant method allows the manufacture of large quantities of crude oligonucleotide with improved purity and increased yield to be carried out quickly, easily, and inexpensively. The following examples are for illustration purposes only and should not be used in any way to limit the appended claims.

EXAMPLES

Methods

Synthesis of the Acrylonitrile-thymidine Adduct:

To a stirred solution of thymidine (0.48 g, 2 mmol), triethylamine (20 ml) and dry pyridine (20 ml) was added freshly distilled acrylonitrile (1 ml, 15 mmol). After heating at 50° C. for 24 hours, the reaction mixture was cooled, concentrated, and purified by flash chromatography using dichloromethane:ethylacetate:methanol (85:15:5) as the mobile phase. Appropriate fractions were collected and concentrated to give the desired adduct as a colorless solid in 47% yield having a m.pt. of 114–116° C. The product exhibited the expected spectroscopic profile in $^1$H NMR and $^{13}$C NMR.

Enzymatic Digestion of the Oligonucleotides:

Both the full length oligonucleotide and the n+ impurity were subjected to enzymatic degradation by snake venom phosphodiesterase and shrimp alkaline phosphatase. One $A_{260}$ OD unit of the oligonucleotide was dissolved in 10 mM Tris-HCl buffer pH 8.2 containing 2 mM $MgCl_2$ and 4 units each of phosphodiesterase and alkaline phosphatase enzymes and incubated at 37° C. for 18 hours. The reaction mixture was then heated at 90° C. for 2 minutes, cooled to room temperature, and analyzed by reversed phase HPLC against authentic nucleoside standards.

Deprotection of Oligonucleotides:

After completion of oligonucleotide synthesis and while the oligonucleotides were still attached to the substrate in the column, a solution of 20% diethylamine in anhydrous acetonitrile was passed through the column at a flow rate of 1 ml/min for 10 minutes to selectively remove the phosphate protecting groups. The column was washed with acetonitrile and the substrate dried in vacuum. This was followed by treating the oligonucleotides with concentrated ammonium hydroxide to remove the oligonucleotides from the substrate and remove the nucleoside protecting groups.

Example 1

Addition of Acrylonitrile on DNA Nucleobases: An oligonucleotide $G_{10}T_{10}$ was synthesized on an Oligo Pilot® II DNA synthesizer using Amersham Pharmacia polymer support 30-HL$^R$. This polystyrene bases substrate was loaded in a 24 ml column and standard phosphoramidite chemistry was used to synthesize the oligonucleotide. The oligomer was cleaved from the substrate and deprotected by treating the substrate with 30% $NH_4OH$ at 65° for 16 hr. Removal of solvent in vacuum afforded the crude oligonucleotide mixture. Ion exchange HPLC of the crude material (DMTr-on) showed the full length product formed in 71% yield along with the presence of 8% n+ impurity (FIG. 1). The crude material was purified on Amersham-Pharmacia AKTA® HPLC purification system. The two oligonucleotide samples were further analyzed by Matrix-Assisted Laser Desorption Ionization-Time Of-Flight/Mass Spectrometry ("MALDI-TOF/MS") to determine their molecular weight. The molecular weight of the full length material ("DMTr-off") was observed to correspond to 6271 mass units, which is in agreement with the calculated value for an oligonucleotide with $G_{10}T_{10}$ sequence. The molecular weight of the isolated n+impurity corresponded to 6327 mass units—a difference of 56 mass units, which is in close agreement with the addition of a cyanoethyl group from the acrylonitrile (53 mass units). LCMS analysis of the n+ impurity showed the molecular weight of this impurity as 6324 mass units, a difference of 53 mass units corresponding to addition of acrylonitrile to thymidine.

Both the full length oligonucleotide and the n+ impurity were subjected to enzymatic degradation by phosphodiesterase and alkaline phosphatase. In this method, a oligonucleotide is treated with a combination of enzymes to break the oligonucleotide into individual nucleoside components which are then analyzed by HPLC. The retention time of the nucleosides in the enzymatic digest is then compared with authentic nucleoside references to determine their relative ratio and the presence of any modified nucleoside product. When the digestion sample obtained from the hydrolysis of the n+ oligonucleotide impurity was analyzed on reversed phase HPLC, the presence of an additional peak eluting in addition to peaks corresponding to thymidine and 2'-deoxyguanosine were observed. This peak was shown to be the $N^3$ cyanoethyl adduct of thymidine when compared with the elution profile of an authentic sample prepared synthetically by a different route.

Example 2

Figure 2:
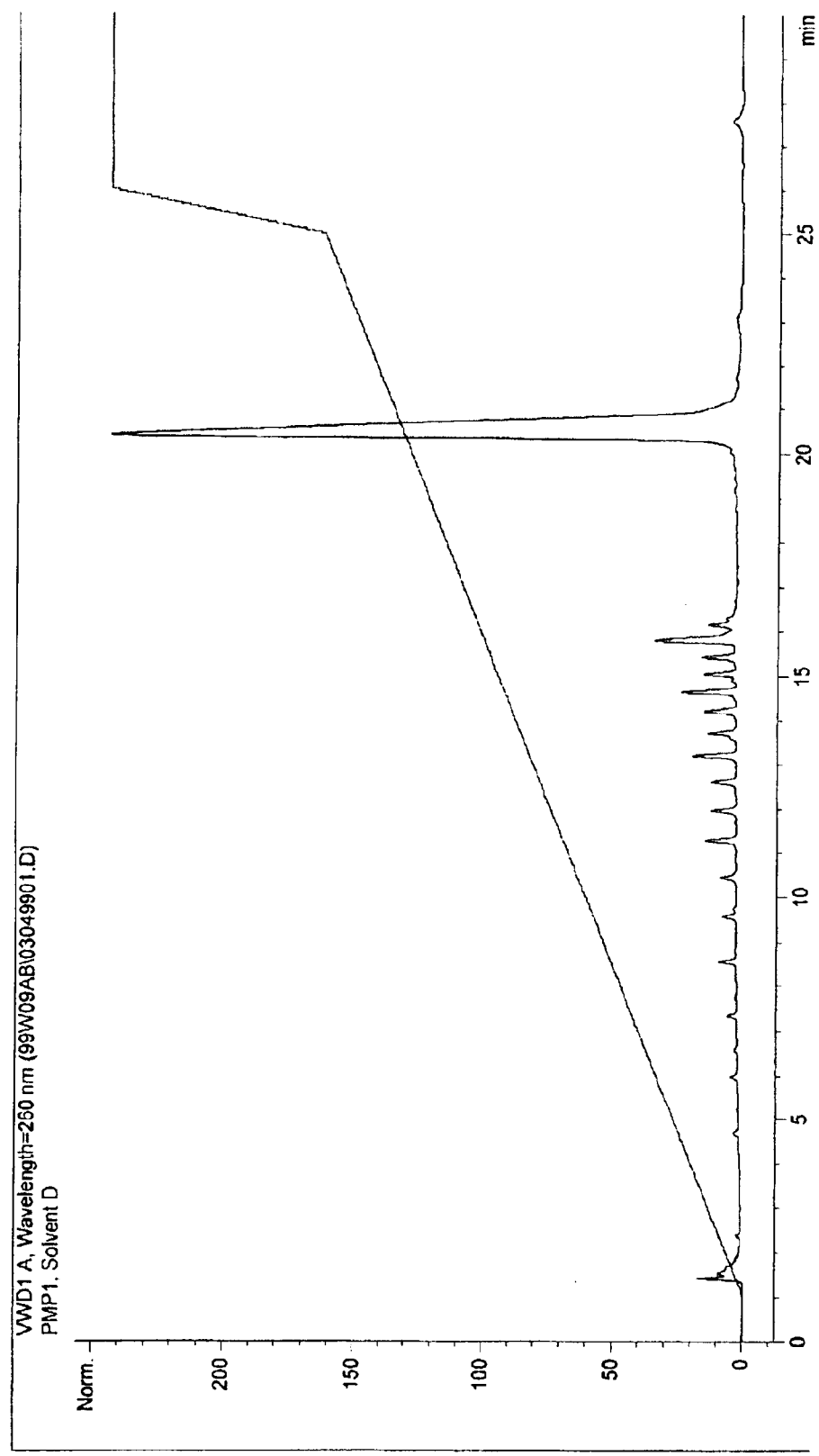
FIG. 2 is a chromatogram of a crude trityl-on oligonucleotide $T_{10}G_{10}$ mixture treated with 20% diethylamine in dry acetonitrile prior to treatment with ammonium hydroxide and separated by HPLC and detected at 260 nm.
Figure 3:
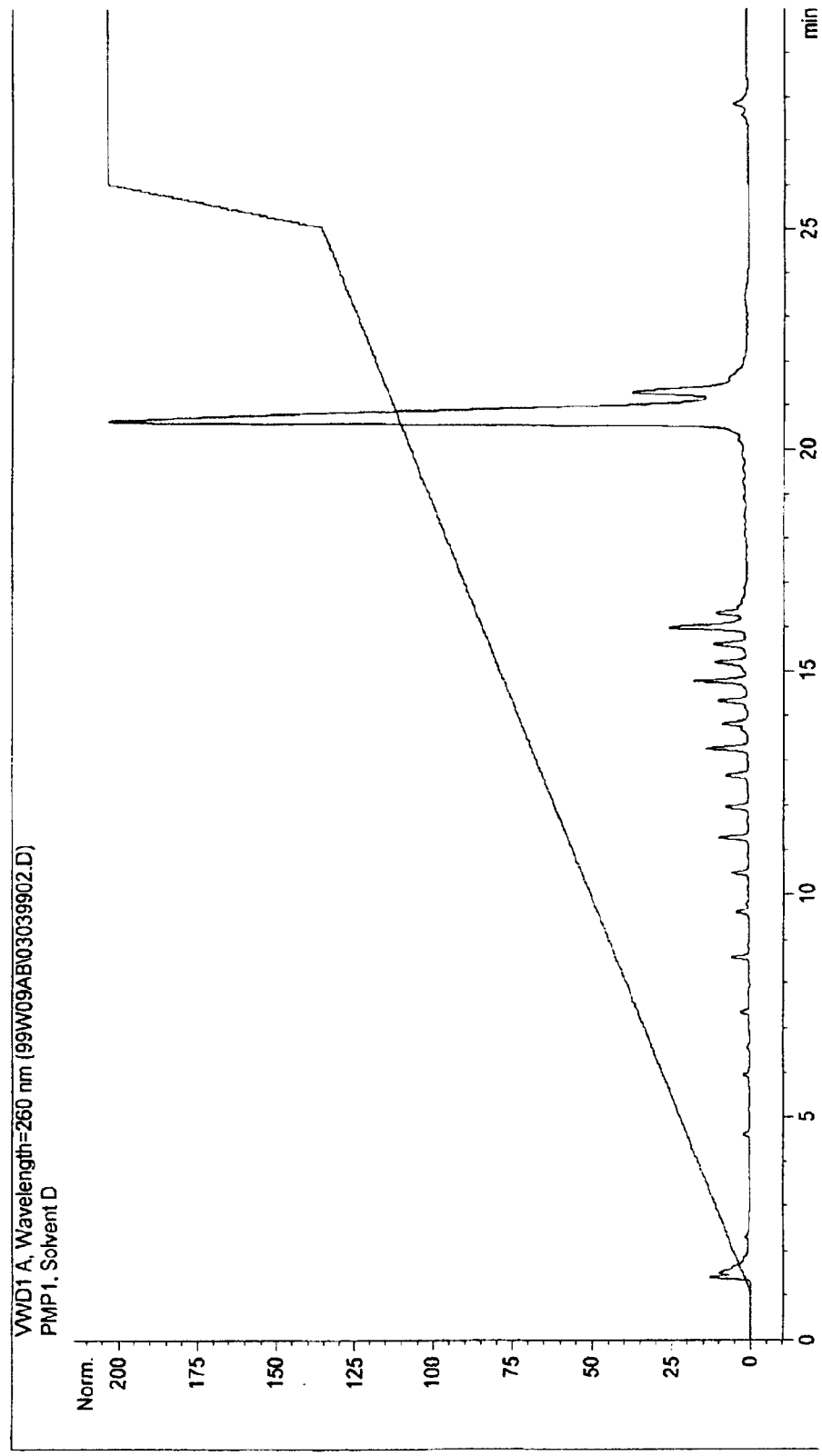
FIG. 3 is a chromatogram of a crude trityl-on oligonucleotide 5'-$NH_2$ —$(CH_2)_6$—$C_7T_{14}$ mixture separated by HPLC and detected at 260 nm.

A number of regular and modified oligonucleotides sequences (including 2'-O-methyl RNA and phosphorothioate oligonucleotides) were synthesized on Oligo Pilot® II using either Amersham Pharmacia polymer support 30-HL® or controlled pore glass ("CPG") as the substrate. All oligonucleotides, while still attached to the substrate in the synthesis column, were treated with a solution of 20% diethylamine in anhydrous acetonitrile for 10 minutes. This was followed by standard deprotection with concentrated ammonium hydroxide. After removal of the volatiles, all the oligonucleotides were analyzed by ion exchange HPLC. The results indicate that all samples that were pre-treated with diethylamine showed significantly less n+ impurity profile in contrast to those that were directly treated with concentrated ammonium hydroxide. The n+ impurity in pretreated oligomers was reduced to less than 0.05 percent with corresponding increase in the yield of the full length oligomer by 3–7% depending on the sequence. For example, a test sequence $T_{10}G_{10}$, when deprotected under standard conditions without diethylamine treatment displaced a HPLC chromatogram indicating the presence of 71% full length product, in addition to ~8% n+ product (FIG. 1). In contrast, the same substrate which was pretreated with diethylamine prior to standard ammonium hydroxide deprotection displaced a HPLC chromatogram showing presence of 78% full length product with almost negligible n+ impurities (FIG. 2).

There was no observed loss of the oligonucleotide from the substrate during the diethylamine treatment. Digestion experiments after deprotection and cleavage from the substrate did not indicate any base modifications even after the oligonucleotide was exposed to twice the amount of time with 20% diethylamine. Identical results were observed in the case of 2'-O-methyl, phosphorothioate and chimeric oligonucleotides. The results are reproducible with different scales of oligonucleotide synthesis and with different lengths of the oligonucleotides.

Example 3

Figure 4:
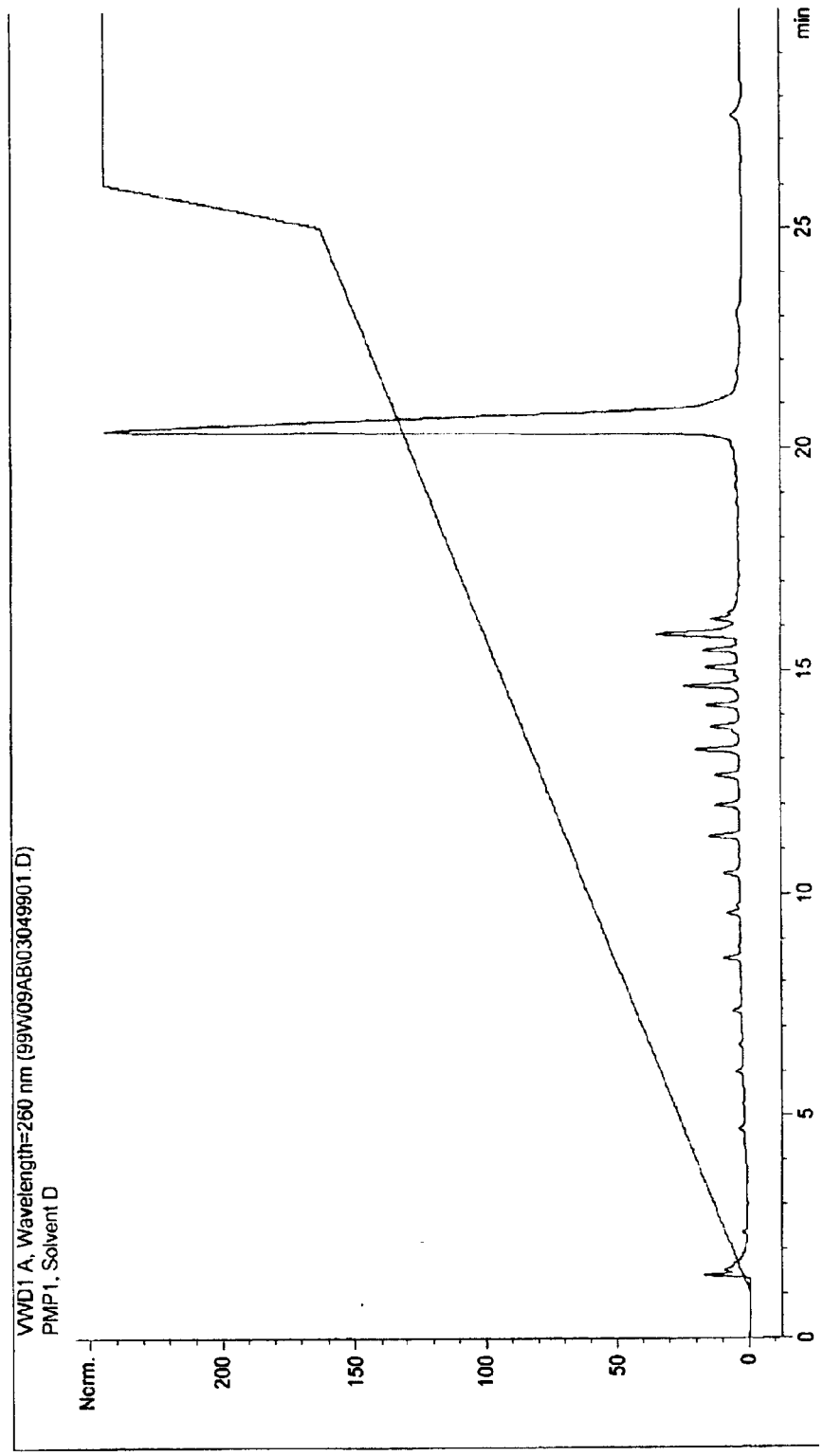
FIG. 4 is a chromatogram of a crude trityl-on oligonucleotide 5'-$NH_2$ —$(CH_2)_6$—$C_7T_{14}$ mixture treated with 20% diethylamine prior to treatment with ammonium hydroxide and separated by HPLC and detected at 260 nm.

Oligonucleotides tethered with linkers bearing amino groups gave clean products with no evidence of amino group modification (FIG. 4). These oligonucleotides are generally synthesized by addition of a protected amino linker amidite on the synthesizer. During standard deprotection with ammonium hydroxide, significant amounts of oligonucleotides get irreversibly modified at the amino group, possibly due to the addition of acrylonitrile. The yield of any post-synthetic modification product involving conjugation of a reporter moiety to the amino group, therefore, gets significantly reduced.

Example 4

The oligonucleotides when treated with an ammonium hydroxide solution containing 50 mmol of dithiothreitol ($HS-CH_2-CHOH-CHOH-CH_2-SH$) to scavenge acrylonitrile formed during deprotection were not able to completely suppress the nucleobase modification as was the case when primary and tertiary amine solutions were used for selective deprotection. All reagents containing ammonium hydroxide solution with dithiothreitol were able to reduce the n+ impurity to a small extent only. In addition, deprotection of the oligonucleotides using gaseous ammonia gave a higher concentration of n+ impurities in the crude oligonucleotide mixture.

Example 5

A number of different oligonucleotides, (regular DNA or 2'-OMe) were synthesized on Oligo Pilot II using either PS HL 30 or CPG as the substrate with different base compositions. All oligonucleotides were treated with 20% diethylamine in anhydrous acetonitrile for 10 minutes while still attached to the substrate in the column. After deprotection and cleavage from the support, the oligonucleotides were analyzed by ion exchange high performance chromatography. The results indicate that the n+ impurity was reduced to less than 0.05% and the yields of the full length material increased. There was no loss of the oligonucleotide during the treatment which was established by collecting the wash separately and analyzing it. Digestion experiments after deprotection and cleavage from the substrate did not indicate any base modifications even after the oligonucleotide was exposed to twice the amount of time with 20% diethylamine. This method was applicable to 2'-OMe oligonucleotides, as well as to amino linked oligonucleotides and were reproducible at various scales of synthesis and different lengths of the oligonucleotide sequences.

Although a number of embodiments are described in detail by the above examples, the instant invention is not limited to such specific examples. Various modifications will be readily apparent to one of ordinary skill in the art and fall within the spirit and scope of the appended claims.

What is claimed is:

1. A method for purifying an oligonucleotide that comprises:
    a) providing an oligonucleotide attached to a substrate, wherein the oligonucleotide contains phosphate protecting groups;
    b) contacting the oligonucleotide with a reagent that cleaves the phosphate protecting groups from the oligonucleotide without detaching the oligonucleotide from the substrate;
    c) isolating the oligonucleotide attached to the substrate from the cleaved phosphate protecting groups; and
    d) cleaving the oligonucleotide from the substrate.

2. The method of claim 1, wherein the substrate is a solid.

3. The method of claim 1, wherein the substrate is a liquid.

4. The method of claim 1, wherein the substrate is an inorganic material, an organic material, or a combination thereof.

5. The method of claim 1, wherein the phosphate protecting group is a group capable of undergoing β-elimination.

6. The method of claim 5, wherein the phosphate protecting group is a 2-cyanoethyl group.

7. The method of claim 1, wherein the reagent cleaves the phosphate protecting group from the oligonucleotide by β-elimination.

8. The method of claim 1, wherein the reagent used to selectively remove phosphate protecting groups is an amine with a formula R—N—$R_1R_2$ wherein R, $R_1$, and $R_2$ are independently hydrogen, hydroxy, or a hydrocarbon selected from the group consisting of alkyl, allyl, aryl, cycloalkyl, alkenyl, alkoxy, allyloxy, and aryloxy, and having from one to twenty carbon atoms.

9. The method of claim 1, wherein the reagent is an organic amine.

10. The method of claim 1, wherein the reagent is diethylamine.

11. The method of claim 1, wherein the reagent contains about 20% v/v diethylamine.

12. The method of claim 1, wherein the reagent is delivered as a gas.

13. A method of claim 1, wherein the oligonucleotide backbone contains at least one phosphodiester linkage.

14. A method of claim 1 wherein the oligonucleotide backbone contains at least one phosphoramidate linkage.

15. A method for purifying an oligonucleotide that comprises:
    a) providing an oligonucleotide containing a phosphate protecting group attached to a substrate, wherein the phosphate protecting group is 2-cyanoethyl;
    b) contacting the oligonucleotide with diethylamine to cleave the phosphate protecting groups from the oligonucleotide without detaching the oligonucleotide from the substrate;
    c) isolating the oligonucleotide attached to the substrate from the cleaved phosphate protecting groups; and
    d) contacting the oligonucleotide attached to the substrate with ammonium hydroxide to cleave the oligonucleotide from the substrate.

* * * * *